US011158436B2

United States Patent
Ruehrig et al.

(10) Patent No.: US 11,158,436 B2
(45) Date of Patent: Oct. 26, 2021

(54) FILTER SYSTEM FOR THE LOCAL ATTENUATION OF X-RADIATION, X-RAY APPARATUS AND METHOD FOR LOCALLY CHANGING THE INTENSITY OF X-RADIATION

(71) Applicant: Siemens Healthcare GmbH, Erlangen (DE)

(72) Inventors: Manfred Ruehrig, Lauf (DE); Oliver Schmidt, Erlangen (DE); Rainer Gransee, Budenheim (DE); Michael Bassler, Mainz (DE); Vishnu Vatheriparambil Mohandas, VD Eindhoven (NL)

(73) Assignee: SIEMENS HEALTHCARE GMBH, Erlangen (DE)

( * ) Notice: Subject to any disclaimer, the term of this patent is extended or adjusted under 35 U.S.C. 154(b) by 45 days.

(21) Appl. No.: 16/814,263

(22) Filed: Mar. 10, 2020

(65) Prior Publication Data

US 2020/0303085 A1    Sep. 24, 2020

(30) Foreign Application Priority Data

Mar. 18, 2019 (EP) .................................. 19163502

(51) Int. Cl.
*G01N 23/00* (2006.01)
*G21K 1/10* (2006.01)
*G01N 23/083* (2018.01)

(52) U.S. Cl.
CPC ............. *G21K 1/10* (2013.01); *G01N 23/083* (2013.01); *G01N 2223/313* (2013.01)

(58) Field of Classification Search
CPC .. A61B 6/06; A61B 6/4035; G01N 2223/313; G01N 23/083; G21K 1/10
See application file for complete search history.

(56) References Cited

U.S. PATENT DOCUMENTS

| 3,755,672 A | 8/1973 | Edholm et al. |
| 4,856,042 A | 8/1989 | Staron et al. |
| (Continued) | | |

FOREIGN PATENT DOCUMENTS

| DE | 102012206953 B3 | 5/2013 |
| JP | H02257942 A | 10/1990 |

OTHER PUBLICATIONS

Extended European Search Report and English translation thereof dated Oct. 8, 2019.
(Continued)

*Primary Examiner* — Dani Fox
(74) *Attorney, Agent, or Firm* — Harness, Dickey & Pierce, P.L.C.

(57) ABSTRACT

A filter system is for the local attenuation of X-radiation. In an embodiment, the filter system includes a filter device, arranged in a beam path of an X-ray apparatus and including a channel arrangement, the channel arrangement including a multiplicity of channel sections extending in parallel on a plane; a supply device to provide a 2-phase fluid flow containing drops of an absorber liquid, to absorb X-radiation and a carrier liquid transparent to X-radiation; and a sorting section, including an input connected to the supply device, a first output connected to the channel arrangement, a second output, and a deflection device to direct individual drops of the absorber liquid to the first output or the second output.

18 Claims, 7 Drawing Sheets

(56) References Cited

U.S. PATENT DOCUMENTS

| | | | |
|---|---|---|---|
| 6,453,012 B2 | 9/2002 | Herbert | |
| 8,876,379 B2* | 11/2014 | DiRisio | A61B 6/447 378/198 |
| 9,431,141 B1 | 8/2016 | Burggraf et al. | |
| 9,966,159 B2 | 5/2018 | van Arendonk et al. | |
| 2013/0287179 A1 | 10/2013 | Fadler et al. | |

OTHER PUBLICATIONS

European Decision to Grant and English translation thereof dated Jan. 15, 2021.

Wang, Meng et al.: "A reconfigurable liquid metal antenna driven by electrochemically controlled capillarity"; Journal of Applied Physics; vol. 117; No. 19; 2015; doi: https://doi.org/10.1063/1.4919605.

RMIT University: "Liquid metal pump a breakthrough for microfluidics"; ScienceDaily; Feb. 21, 2014; https://www.sciencedaily.com/releases/2014/02/140221073833.htm.

Venere, Emil: "Inkjet-printed liquid metal could bring wearable tech, soft robotics"; Apr. 7, 2015; https://phys.org/news/2015-04-inkjet-printed-liquid-metal-wearable-tech.html.

Vetrovec, John et al.: "Liquid metal heat sink for high-power laser diodes"; Proceedings of SPIE; vol. 8605; 2013; doi: https://doi.org/10.1117/12.2005357.

Hutter, T. et. al., "Formation of Spherical and Non-Spherical Eutectic Gallium-Indium Liquid-Metal Microdroplets in Microfluidic Channels at Room Temperature", Adv. Funct. Mater., DOI: 10.1002/adfm.201200324, 2012.

Gough, Ryan et al.: "Continuous Electrowetting of Non-toxic Liquid Metal for RF Applications"; IEEE Access; vol. 2; pp. 874-882; 2014; DOI: 10.1109/ACCESS.2014.2350531.

Tian, Lu et al.: "A Microfluidic Chip for Liquid Metal Droplet Generation and Sorting"; Micromachines; vol. 8; 2017; DOI: https://doi.org/10.3390/mi8020039.

European Search Report for European Application No. 19163502.8 dated Oct. 8, 2019.

\* cited by examiner

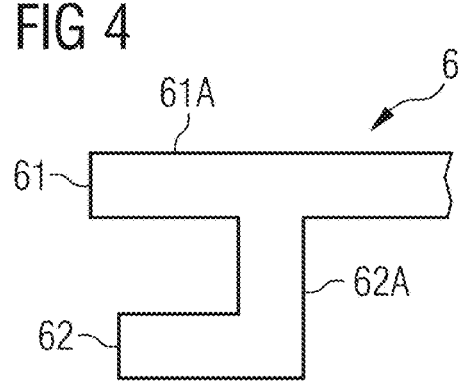
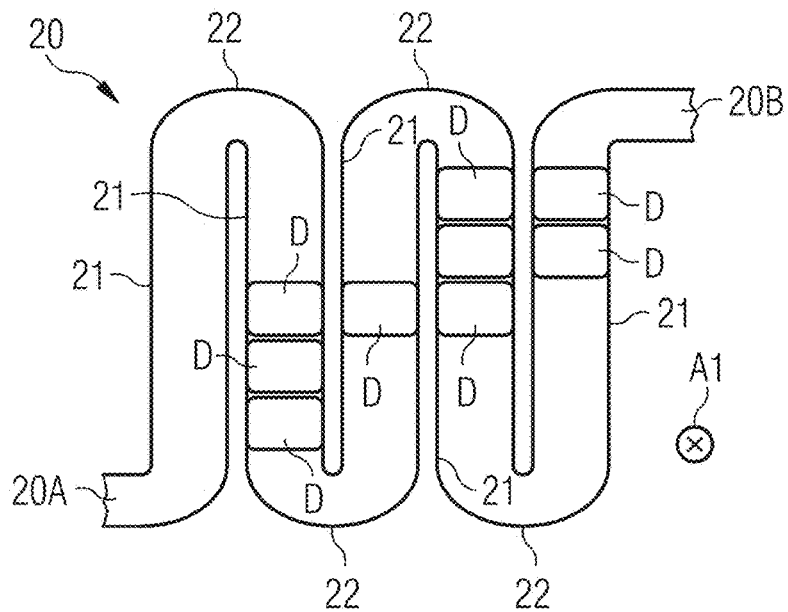
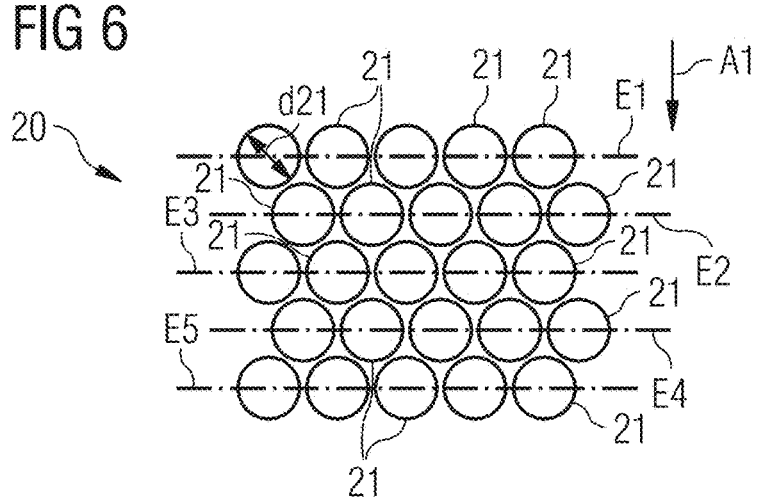

FILTER SYSTEM FOR THE LOCAL ATTENUATION OF X-RADIATION, X-RAY APPARATUS AND METHOD FOR LOCALLY CHANGING THE INTENSITY OF X-RADIATION

PRIORITY STATEMENT

The present application hereby claims priority under 35 U.S.C. § 119 to European patent application number EP 19163502.8 filed Mar. 18, 2019, the entire contents of which are hereby incorporated herein by reference.

FIELD

Embodiments of the invention generally relate to a filter system for the local attenuation of X-radiation, an X-ray apparatus and a method for locally changing the intensity of X-radiation.

BACKGROUND

During X-ray examinations of patients, X-radiation is directed at the region to be examined in the body of the patient. In this context, the situation can occur that the region to be examined has locally differing absorption characteristics for X-rays. For example, soft tissue, organs and bones each have different absorption characteristics. As a consequence, those regions of interest for the medical examination might not be very clearly visible within an X-ray scan.

In consideration of the above, and in order to limit as far as possible a radiation dose for the patient during the examination, use is generally made of X-ray filters for local attenuation of the X-radiation. For example, DE 10 2012 206 953 B3 describes an X-ray filter which is arranged in the beam path of an X-ray apparatus, comprising a liquid that absorbs X-radiation and is arranged between a membrane and a cover plate, wherein a layer thickness of the liquid can be changed locally via control elements in order to adjust the attenuation of the radiation locally.

U.S. Pat. No. 3,755,672 A describes an X-ray filter with an absorber liquid which is arranged between two plates, wherein one of the plates is flexible and a distance between the plates can be varied via servomotors. U.S. Pat. No. 9,966,159 B2 describes an X-ray filter in which an absorber liquid is displaced via electrical forces using an electrode arrangement in order to open a beam path locally. U.S. Pat. No. 6,453,012 B2 describes an X-ray apparatus with a filter system which comprises a filter device having a plurality of filter elements in the form of tubes that extend in the direction of radiation. The tubes are filled from one end with an absorber liquid in order to locally adjust an attenuation of the radiation by way of so-called "electrowetting".

U.S. Pat. No. 4,856,042 A further describes an X-ray filter with a chamber that is formed between an upper and a lower plate, in which separating walls are so arranged as to extend radially from an opening of the lower plate. Alcohol can be supplied to the chamber through the opening. Mercury can be supplied to the chamber through a nozzle at a radial edge region, such that part-spaces which are separated from each other by the separating walls can be filled in some cases with alcohol and in some cases with mercury in a radial direction.

The publication JP H02 257942 A describes a radiation filter in FIG. 3, comprising a plurality of parallel tubular bodies containing mercury, wherein a region containing a liquid that allows radiation to pass is arranged between two regions that contain mercury. The mercury or the region containing a liquid that allows radiation to pass and is arranged between the mercury regions can be moved by changing a cross section at the end of the respective tube body via a piezoelectric element within the tube body.

SUMMARY

In consideration of the above, an improved design for an X-ray filter is desired, particularly an X-ray filter having a simple structure.

Advantageous embodiments are specified in the claims.

According to a first embodiment of the invention, a filter system is provided for the local attenuation of X-radiation. The filter system comprises a filter device, which is arranged in the beam path of an X-ray apparatus and has a channel arrangement with a multiplicity of channel sections extending parallel to each other on a plane, and a supply device for providing a 2-phase fluid flow, said flow containing drops of an absorber liquid which absorbs X-radiation and a carrier liquid that is transparent to X-radiation.

According to a second embodiment of the invention, provision is made for an X-ray apparatus. The X-ray apparatus comprises an X-ray source for generating and emitting X-radiation in a beam path, an X-ray detector which is arranged in the beam path, and a filter system according to the first embodiment, wherein the filter device is arranged in the beam path between X-ray source and X-ray detector. For example, the filter device can be arranged in the beam path in such a way that the channel sections extend transversely relative to the beam path.

According to a third embodiment of the invention, provision is made for a method for locally changing the intensity of X-radiation. The method can be performed in particular using a system according to the first embodiment of the invention and an X-ray apparatus according to the second embodiment of the invention. The method comprises generating predetermined sequences of drops from a 2-phase fluid flow containing drops of an absorber liquid which absorbs X-radiation and a carrier liquid that is transparent to X-radiation, and supplying said drop sequences into channel sections of a channel arrangement of a filter device which is arranged in a beam path between an X-ray source and an X-ray detector, wherein the channel arrangement has a multiplicity of channel sections extending parallel to each other on a plane. The advantages cited in respect of the system and the X-ray apparatus apply to the method likewise.

According to a further example, provision is made for a filter system for the attenuation of X-radiation, comprising a filter device, which is arranged in the beam path of an X-ray apparatus and has two plates that are arranged parallel to each other and define an intermediate space, and a supply device for providing a 2-phase fluid flow containing drops of an absorber liquid that absorbs X-radiation and a carrier liquid that is transparent to X-radiation, said supply device being connected to the intermediate space. The filter system optionally also comprises a sorting section with an input that is connected to the supply device, a first output that is connected to the intermediate space, a second output, and a deflection device for directing individual drops of the absorber liquid to the first output or the second output. The optional sorting section and the supply device can be developed as described above.

According to another embodiment of the invention, provision is made for a filter system for local attenuation of X-radiation, comprising:

a filter device, arranged in a beam path of an X-ray apparatus and including a channel arrangement, the channel arrangement including a multiplicity of channel sections extending in parallel on a plane;

a supply device to provide a 2-phase fluid flow containing drops of an absorber liquid, to absorb X-radiation and a carrier liquid transparent to X-radiation; and a sorting section, including an input connected to the supply device, a first output connected to the channel arrangement, a second output, and a deflection device to direct individual drops of the absorber liquid to the first output or the second output.

According to another embodiment of the invention, provision is made for an X-ray apparatus, comprising:

an X-ray source to generate and emit X-radiation in a beam path;

an X-ray detector, arranged in the beam path; and the filter system of an embodiment, wherein the filter device of the filter system is arranged in the beam path, between the X-ray source and the X-ray detector.

According to another embodiment of the invention, provision is made for a method for locally changing the intensity of X-radiation, the method comprising:

generating sequences of drops from a 2-phase fluid flow containing drops of an absorber liquid, to absorb X-radiation and a carrier liquid, transparent to X-radiation; and supplying the drop sequences generated into channel sections of a channel arrangement of a filter device, arranged in a beam path between an X-ray source and an X-ray detector, wherein the channel arrangement includes a multiplicity of channel sections extending in parallel on a plane.

BRIEF DESCRIPTION OF THE DRAWINGS

In general, the features and advantages disclosed in connection with one embodiment of the invention or example of the disclosure are also disclosed for the other embodiments of the invention or examples of the disclosure.

The invention is explained in greater detail below with reference to example embodiments and with the aid of figures, in which:

FIG. 4 shows a schematic sectional illustration of a drop generator of the filter system from FIG. 3;

FIG. 5 shows a schematic illustration of a channel arrangement of a filter device of a filter system according to an example embodiment of the present invention in a plan view;

FIG. 6 shows a schematic sectional illustration of the channel arrangement from FIG. 5;

DETAILED DESCRIPTION OF THE EXAMPLE EMBODIMENTS

Figure 1:
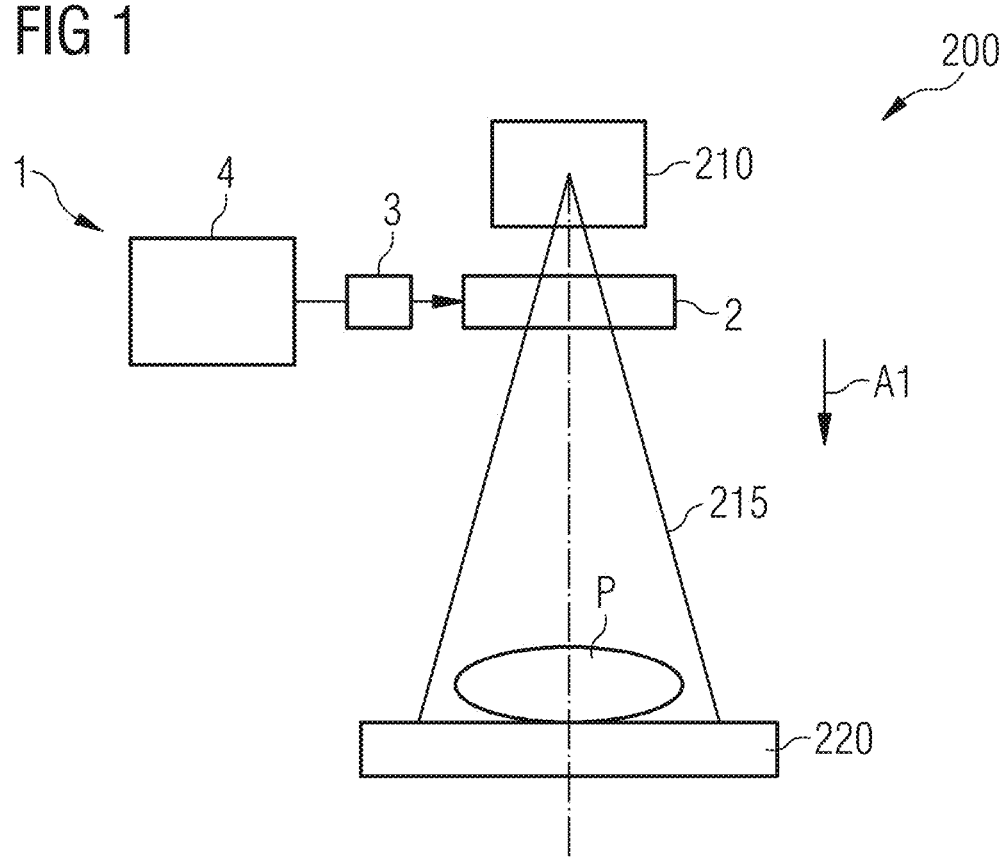
FIG. 1 shows a schematic illustration of an X-ray apparatus according to an example embodiment of the present invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/ DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to a first embodiment of the invention, a filter system is provided for the local attenuation of X-radiation. The filter system comprises a filter device, which is arranged in the beam path of an X-ray apparatus and has a channel arrangement with a multiplicity of channel sections extending parallel to each other on a plane, and a supply device for providing a 2-phase fluid flow, said flow containing drops of an absorber liquid which absorbs X-radiation and a carrier liquid that is transparent to X-radiation.

A concept underlying at least one embodiment of the invention resides in generating a specific sequence of liquid drops of an absorber material which absorbs X-radiation and liquid drops of a carrier material which allows X-radiation to be transmitted and cannot be mixed with the absorber material, positioning this sequence of drops in a planar channel system, and arranging the channel system in the beam path of an X-ray apparatus. The X-rays are thereby wholly or partially absorbed or attenuated at those points of the channel system at which drops of absorber material are arranged.

For the purpose of positioning the drops in the beam path, provision is made for a filter device with a channel arrangement. The channel arrangement has a planar extent, which is defined by a multiplicity of adjacently arranged channel sections running in parallel. Each channel section can be supplied with a drop sequence which is predetermined in relation to the longitudinal extent of the respective channel section. For this purpose, the channel arrangement is connected to a supply device.

The supply device delivers a two-phase fluid flow, in which one phase is formed by drops of absorber liquid and the other phase by drops of carrier liquid. One advantage of the invention is that the filter device with the channel arrangement, which is intended to be arranged in the beam path, has a very simple design format and includes essentially hydraulic line structures.

According to a further embodiment variant of the filter system, provision is made for the supply device to have a first reservoir containing the absorber liquid, a second reservoir containing the carrier liquid, and a drop generator for generating the 2-phase fluid flow, wherein the drop generator is connected via a first input to the first reservoir, via a second input to the second reservoir, and via an output to the channel arrangement. According to this embodiment variant, the individual drops from which the 2-phase fluid flow is composed are generated by a drop generator, this being configured to cut off a first fluid flow of absorber liquid and a second fluid flow of carrier liquid alternately, in order thus to generate a desired and optionally periodic drop sequence. The drop sequence can conceivably be generated with drops of different length, in order to provide the desired sequence of drops with reference to an absorption pattern. It is also possible to generate periodic drop sequences with drops of essentially the same size and regular intervals, which are then sorted according to the desired absorption pattern by a sorting section which is connected to the output of the drop generator as described below.

According to an embodiment variant, the drop generator can have a first line section comprising the first input and a second line section comprising the second input, said first and the second line sections merging with each other in a T-shaped junction. Therefore the drop generator is embodied as a T-piece, to which absorber liquid is supplied at a first input and carrier liquid is supplied at a second input. A particularly simple format can be achieved thereby. Optionally, the drop generator can also have a first valve connected to the first input first and a second valve connected to the second input, wherein the valves can each be switched between an open state and a closed state in order to interrupt or allow the fluid throughput in each case. For example, the valves can be embodied as magnetic valves. Adjustment of the drop size is simplified by the valves.

According to a further embodiment variant of the filter system, provision is made for the supply device to have a reservoir with an emulsion of drops of the absorber liquid and the carrier liquid, and for the reservoir to be connected to the input of the sorting section. For example, a stabilizer such as e.g. PEG (polyethylene glycol) or silicone oil from which oxygen has been removed can be added to the carrier liquid for this purpose. The provision of an emulsion in a reservoir further simplifies the format of the filter system.

According to an embodiment of the invention, provision is made for the filter system to have a sorting section with an input that is connected to the supply device, a first output that is connected to the channel arrangement, a second output, and a deflection device for directing individual drops of the absorber liquid to the first output or the second output. The 2-phase fluid flow provided by the supply device is supplied to the sorting section, which is designed to separate individual drops, in particular drops of absorber liquid, out of the fluid flow. For this purpose, the sorting section has a deflection device for applying a force to the drops, said force being transverse to the direction of flow, such that the drops are supplied either to a first output which is connected in a fluidically conductive manner to the channel arrangement, or to a second output which is not connected to the channel arrangement but to e.g. a reservoir. In this way, it is possible to generate specific drop sequences efficiently. For example, the deflection device can have a first electrode and a second electrode arranged opposite thereto, in order to generate an electrical field for deflecting the drops in a separation section which extends between the input and the outputs of the sorting section. Alternatively, the deflection device can also be designed to generate a pressure pulse in order to deflect the individual drops.

Via the sorting section, it is possible to generate almost any desired drop sequences and hence absorption patterns for local attenuation of the X-radiation in an efficient manner. The regions in which the X-radiation is to be attenuated can therefore be selected in a flexible manner.

According to an embodiment variant of the filter system, provision is made for the channel sections of the channel arrangement to be connected to each other via connecting sections in such a way that they form a continuous channel. The optional sorting section can be connected via its first output to an input of the channel in particular. Accordingly, each channel section is connected at its end to a further, adjacent channel section via a connecting section which is e.g. U-shaped. A meandering continuous channel with parallel channel sections is thus formed. This has the advantage that the whole channel arrangement or each individual channel section of the channel arrangement can be filled with a drop pattern via a single sorting section. This further simplifies the format of the filter system.

Alternatively, the channel sections of the channel arrangement can each be formed by individual channels which are each connected to the supply device. In this case, the filter system can have a number of sorting sections which corresponds to the number of channel sections, wherein each channel of the channel arrangement is connected in each case to a first output of a respective sorting section. Therefore the channel arrangement is formed by a multiplicity of individual separate channels or lines, and each channel is connected to the supply device directly or is optionally connected to the supply device via a sorting section which is assigned to the channel in each case. This layout has the advantage that all channel sections of the channel arrangement can be filled with drop sequences simultaneously.

According to a further embodiment variant of the filter system, provision is made for a first group of channel sections of the channel arrangement to be arranged on a first plane and for one or more further groups of channel sections to be provided, each of these being arranged on planes which are parallel to the first plane. The channel arrangement can therefore have a plurality of groups of channel sections extending in parallel, the channel sections of a respective group extending on a plane in each case, and the planes being parallel to each other. For example, between two and ten groups of channel sections may be provided. This has the advantage that the degree of attenuation of the radiation can be adjusted by arranging droplets of absorption liquid such that they overlap on the different planes.

According to a further embodiment variant, the channel arrangement has at least two plates which abut each other at their surfaces, wherein grooves defining the channel sections are formed on the surfaces in each case. In particular, a first plate has first grooves on a first surface, a second plate has second grooves on a second surface, and said second grooves run in a manner which corresponds to the first grooves, wherein the first surface of the first plate abuts the second surface of the second plate. A simple design format is thus realized for the channel arrangement. For example, by way of this format it is also possible advantageously to realize a channel arrangement having channel sections on a plurality of planes. The plates can be made of a plastic material such as e.g. PMMA (polymethyl methacrylate), glass or other material which is largely transparent to X-radiation.

According to an embodiment variant, mercury or Galinstan is used as an absorber liquid. The carrier liquid can be in particular an oil, e.g. silicone oil.

For the purpose of transporting the drops, or the 2-phase fluid flow generally, into and out of the channel arrangement, provision can be made for e.g. hydraulic pressure generating devices such as pumps and optionally valves. For example, the reservoir containing the emulsion or the reservoir containing carrier liquid and the reservoir containing absorber liquid can be connected in each case via a pump to the input of the sorting section or of the drop generator. Alternatively, it is also conceivable to equip the channel sections with an electrode arrangement for this purpose, wherein a group of first electrodes is so arranged as to be distributed along the channel sections in an electrically insulating manner, and at least one second electrode in each case is provided in a channel section in each case. The second electrode can be grounded. The first electrodes can be connected to an electrical voltage source consecutively in a temporal sequence. If an electrolyte is added to the carrier liquid or if the absorber liquid is electrically conductive, it is then possible to apply the principle known as "electrowetting" for the purpose of transporting drops in the channel sections. Alternatively, it is also conceivable to generate a wandering electrical field along the channel sections via an electrode arrangement, and to move the drops of absorber liquid via electrostatic forces. Generally, a transport device which is coupled to the channel sections can be provided for the purpose of transporting the 2-phase fluid flow.

According to a second example of the disclosure, a filter system for the attenuation of X-radiation is provided, comprising a filter device, which is arranged in the beam path of an X-ray apparatus and has a channel arrangement with a multiplicity of channels extending parallel to each other on a plane, a reservoir containing an absorber liquid which absorbs X-radiation, wherein the channels are connected to the reservoir at opposite ends in each case, and a transport system for the transportation of absorber liquid in the channels.

A concept underlying this example resides in achieving a simple format of a filter device via individual channels which extend in parallel, and in filling these channels from opposite sides with liquid columns of an absorber fluid such as e.g. Galinstan or mercury. It is consequently possible using a very simple design format to effect a local attenuation of the X-radiation via the liquid columns of absorber liquid.

According to this example, the channel arrangement is formed by a multiplicity of individual separate channels or lines. Each of the channels is connected to the reservoir in a fluidically conductive manner via a first end and a second end which is positioned opposite thereto. This layout has the advantage that all channel sections of the channel arrangement can be filled with absorber fluid from opposites sides simultaneously.

According to an embodiment variant of this example, provision is made for the absorber liquid to have an electrically conductive component, wherein the transport system has an electrode arrangement with a multiplicity of electrodes arranged along the channels and a switch device which is designed to connect the electrodes individually in each case to an electrical voltage source. Provision is therefore made for transporting the absorber liquid via electrical forces, e.g. via electrostatic forces or by way of so-called "electrowetting".

The phenomenon of the electrowetting is based on varying a contact angle between a liquid, here the absorber liquid, and a surface, here the surface of the channel, by applying an electrical potential. For example, a surface voltage gradient can be electrically induced over the length of a liquid metal slug which is situated between electrolytic liquids, whereby Marangoni forces are generated along the liquid-liquid boundary surface and a movement of the slug is provoked. However, the liquid itself can also be electrically conductive. For the purpose of transporting the absorber liquid in the channels, the electrode arrangement can have e.g. a multiplicity of first electrodes, which are arranged along the individual channels and are electrically insulated from the absorber liquid, e.g. by virtue of the channels being made of electrically insulating material and the electrodes being fastened to an outer surface of the channels. The first electrodes apply a first electrical potential to the channel walls. A second electrode is arranged in the interior of the channels and applies a second electrical potential to the absorber liquid. The switch device connects the individual first electrodes consecutively to the voltage source, whereby transportation of the absorber fluid along the channels is achieved.

For the purpose of transportation by way of electrostatic forces, a multiplicity of opposing first and second electrodes can be distributed along the longitudinal extent of each channel, such that these form a capacitor when a voltage is applied. By connecting the electrodes consecutively to a voltage source, a moving electrical field can be generated along a respective channel 123 in order to transport the absorber liquid.

According to a further embodiment variant of this example, provision is made for the transport system to take the form of a hydraulic system comprising at least one pump, this being arranged between the reservoir and the channel arrangement.

According to a further embodiment variant of this example, a first group of channels is arranged on a first plane and one or more further groups of channels are each arranged on planes parallel to the first plane. The channel arrangement can therefore have a plurality of groups of channels extending in parallel, the channels of a respective group extending on a plane in each case, and the planes being parallel to each other. For example, between two and ten groups of channels may be provided. This has the advantage that the degree of attenuation of the radiation can be adjusted by arranging the liquid columns of absorption liquid such that they overlap or have different lengths on the different planes.

According to a further embodiment variant of this example, the channel arrangement has at least two plates which abut each other at their surfaces, wherein grooves defining the channel sections are formed on the surfaces in each case. In particular, a first plate has first grooves on a first surface, a second plate has second grooves on a second surface, and said second grooves run in a manner which corresponds to the first grooves, wherein the first surface of the first plate abuts the second surface of the second plate. A simple design format is thus realized for the channel arrangement. For example, by way of this format it is also possible advantageously to realize a channel arrangement having channel sections on a plurality of planes. The plates can be made of a plastic material such as e.g. PMMA (polymethyl methacrylate), glass or other material which is largely transparent to X-radiation.

According to both the first embodiment of the invention and the second example of the disclosure, the channel sections of the channel arrangement of the filter device can have in particular a diameter in a range between 50 µm and 5 mm, preferably between 500 µm and 3 mm. The cross-sectional shape of the channel sections can be circular. If the cross-sectional shape is not circular, the diameter of the channel section is understood to be the diameter of a circle which has the same cross-sectional area as the respective channel section.

According to a second embodiment of the invention, provision is made for an X-ray apparatus. The X-ray apparatus comprises an X-ray source for generating and emitting X-radiation in a beam path, an X-ray detector which is arranged in the beam path, and a filter system according to the first embodiment, wherein the filter device is arranged in the beam path between X-ray source and X-ray detector. For example, the filter device can be arranged in the beam path in such a way that the channel sections extend transversely relative to the beam path.

According to a third embodiment of the invention, provision is made for a method for locally changing the intensity of X-radiation. The method can be performed in particular using a system according to the first embodiment of the invention and an X-ray apparatus according to the second embodiment of the invention. The method comprises generating predetermined sequences of drops from a 2-phase fluid flow containing drops of an absorber liquid which absorbs X-radiation and a carrier liquid that is transparent to X-radiation, and supplying said drop sequences into channel sections of a channel arrangement of a filter device which is arranged in a beam path between an X-ray source and an X-ray detector, wherein the channel arrangement has a multiplicity of channel sections extending parallel to each other on a plane. The advantages cited in respect of the system and the X-ray apparatus apply to the method likewise.

According to a further example, provision is made for a filter system for the attenuation of X-radiation, comprising a filter device, which is arranged in the beam path of an X-ray apparatus and has two plates that are arranged parallel to each other and define an intermediate space, and a supply device for providing a 2-phase fluid flow containing drops of an absorber liquid that absorbs X-radiation and a carrier liquid that is transparent to X-radiation, said supply device being connected to the intermediate space. The filter system optionally also comprises a sorting section with an input that is connected to the supply device, a first output that is connected to the intermediate space, a second output, and a deflection device for directing individual drops of the absorber liquid to the first output or the second output. The optional sorting section and the supply device can be developed as described above.

According to this example, it is intended to distribute the drops of absorber liquid in the intermediate space between the plates by way of electrowetting. For the purpose of transporting the drops of absorber liquid in the intermediate space, an electrode arrangement can have e.g. a multiplicity of first electrodes which are arranged in the form of a matrix or an array on one of the plates and are electrically insulated from the absorber liquid, e.g. by virtue of the plates being made of electrically insulating material and the electrodes being fastened to an outer surface of one of the plates. The first electrodes apply a first electrical potential to the plate. One or more second electrodes are arranged in the intermediate space and apply a second electrical potential to the drops of absorber liquid. A switch device connects the individual first electrodes consecutively to an electrical voltage source, whereby transportation of the drops of absorber liquid within the intermediate space is achieved.

A concept underlying this example resides in distributing the drops of absorber liquid in the manner of pixels over a surface, by transporting and arranging them within an intermediate space that is formed between two plates by way of electrowetting. The carrier fluid here can take the form of an electrolytic liquid, for example.

FIG. 1 schematically shows an X-ray apparatus 200. The X-ray apparatus 200 has an X-ray source 210 for generating and emitting X-radiation in a beam path 215, an X-ray detector 220 which is arranged in the beam path 215, and a filter system 1 for the local attenuation of the X-radiation. As further illustrated schematically in FIG. 1, the filter system 1 has a filter device 2, a supply device 4 and an optional sorting section 3. The filter device 2 is arranged in the beam path 215 between the X-ray source 210 and the X-ray detector 220. As symbolically illustrated by the arrow A1 in FIG. 1, the X-radiation generated by the X-ray source 210 penetrates the filter device 2 first, followed by a patient P and then strikes the X-ray detector 220. The filter device 2 serves to attenuate the X-radiation locally, in order to irradiate different regions of the patient P with a different radiation intensity.

Figure 2:
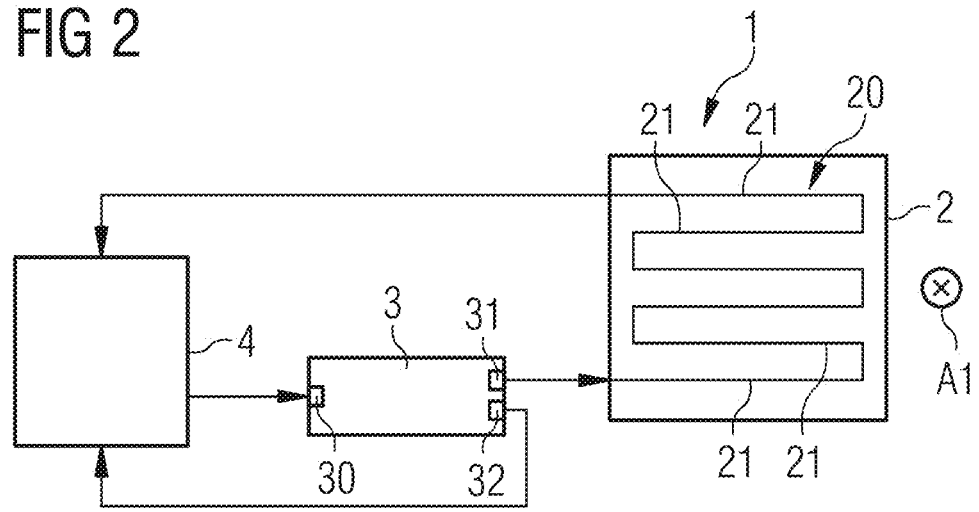
FIG. 2 shows a schematic illustration in the form of a functional block diagram of a filter system according to an example embodiment of the present invention.
Figure 3:
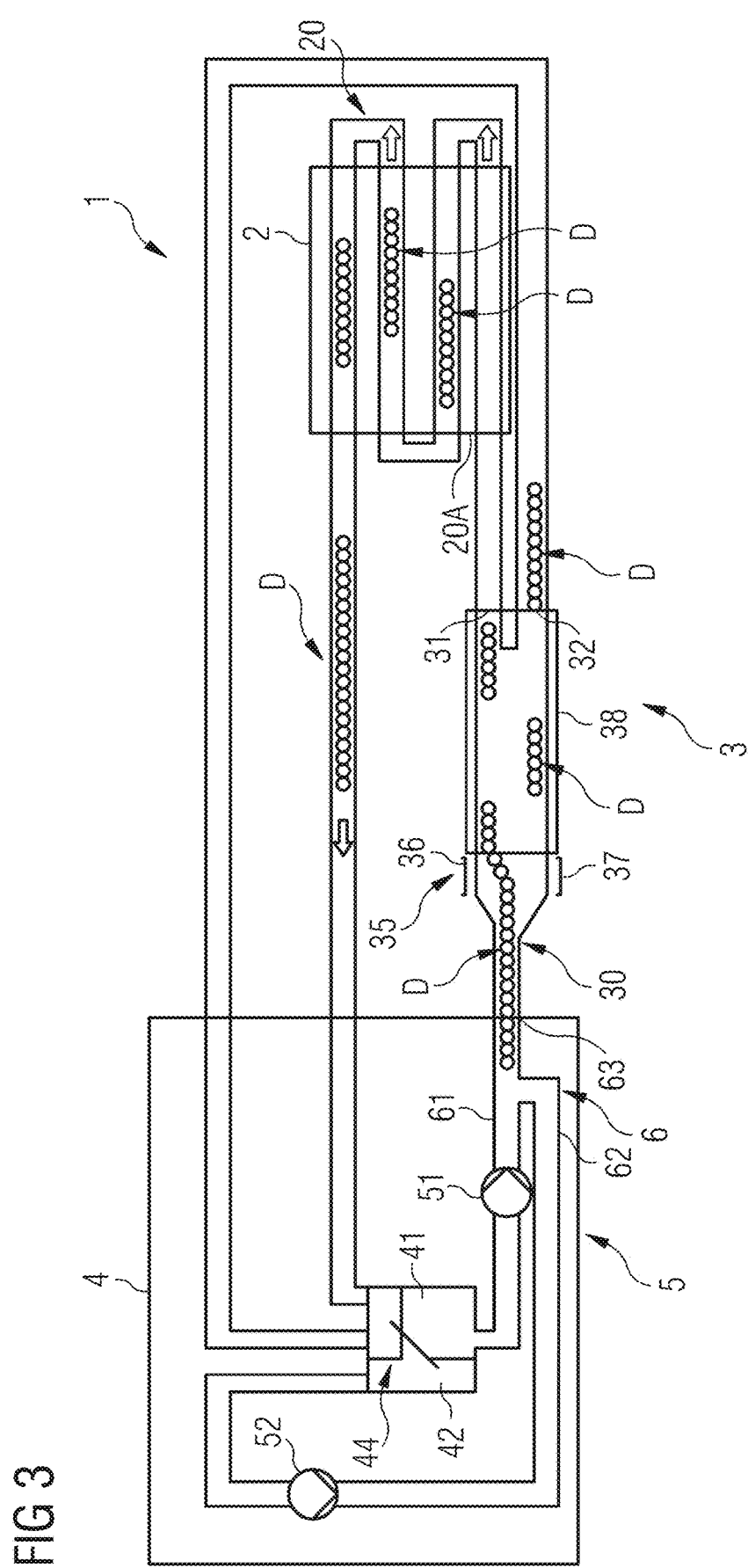
FIG. 3 shows a schematic illustration in the form of a functional block diagram of a filter system according to a further example embodiment of the present invention.

FIG. 2 shows the filter system 1 as a schematic block diagram or a simplified hydraulic flow diagram. FIG. 3 shows a hydraulic flow diagram of the filter system with a greater level of detail. As illustrated in FIG. 2, the filter system 1 comprises a filter device 2, a supply device 4 and an optional sorting section 3.

The filter device 2 has a planar channel arrangement 20 with a multiplicity of channel sections 21 extending parallel to each other on a plane. As illustrated schematically in FIG. 1 and as shown by the directional cross A1 in FIG. 1, the filter device 2 can be arranged in particular in the beam path 215 in such a way that the channel arrangement 20 extends transversely relative to the beam path 215.

An example channel arrangement 20 is illustrated in plan view in FIGS. 2, 3 and 5. It can be seen in FIG. 5 in particular that the parallel channel sections 21 of the channel arrangement 20 can be connected to each other at their ends via connecting sections 22, these being e.g. U-shaped, such that a continuous channel is formed. The channel arrangement 20 can therefore be developed as a continuous channel of parallel, preferably straight, channel sections 21 and connecting sections 22 in the form of an planar meander.

FIG. 6 shows a schematic sectional view of a meandering channel arrangement 20. As illustrated by way of example in FIG. 6, the channel sections 21 can each have a circular cross section. A diameter d21 of the channel sections 21 can generally lie between 50 µm and 5 mm. As further illustrated by way of example in FIG. 6, a first group of the channel sections 21 of the channel arrangement 20 is arranged on a first plane E1, a second group of the channel sections 21 of the channel arrangement 20 is arranged on a second plane E2, a third group of the channel sections 21 of the channel arrangement 20 is arranged on a third plane E3, a fourth group of the channel sections 21 of the channel arrangement 20 is arranged on a fourth plane E4, and a fifth group of the channel sections 21 of the channel arrangement 20 is arranged on a fifth plane E5. The planes E1-E5 extend parallel to each other here. In general, provision can be made for one or more further groups of channel sections 21 which are arranged in each case on planes E2-E5 that are parallel to the first plane E1. In this context, the channel sections 21 of one plane can optionally be so arranged as to be offset relative to the channel sections 21 of the adjacent planes, in a direction transverse to the longitudinal extent of the channel sections 21. The channel sections 21 within each plane E1-E5 are connected via connecting sections 22 as illustrated by way of example in FIG. 5. It is optionally also possible to provide for a given channel section 21 of one plane to be connected via a connecting section 22 to a channel section 21 of a further plane, thereby forming a channel which extends continuously on all planes E1-E5.

The channel sections 21 and, if applicable, connecting sections 22 can take the form of tubes of plastic material as illustrated schematically in FIGS. 5 and 6 by way of example. Alternatively, it is also conceivable for the channel arrangement 20 to be formed by at least two plates 25 which abut each other at their surfaces 25a, 25b, wherein grooves 26 defining the channel sections 21 are formed on the surfaces 25a, 25b in each case, as illustrated by way of example in FIG. 9 and explained in detail below.

Figure 7:
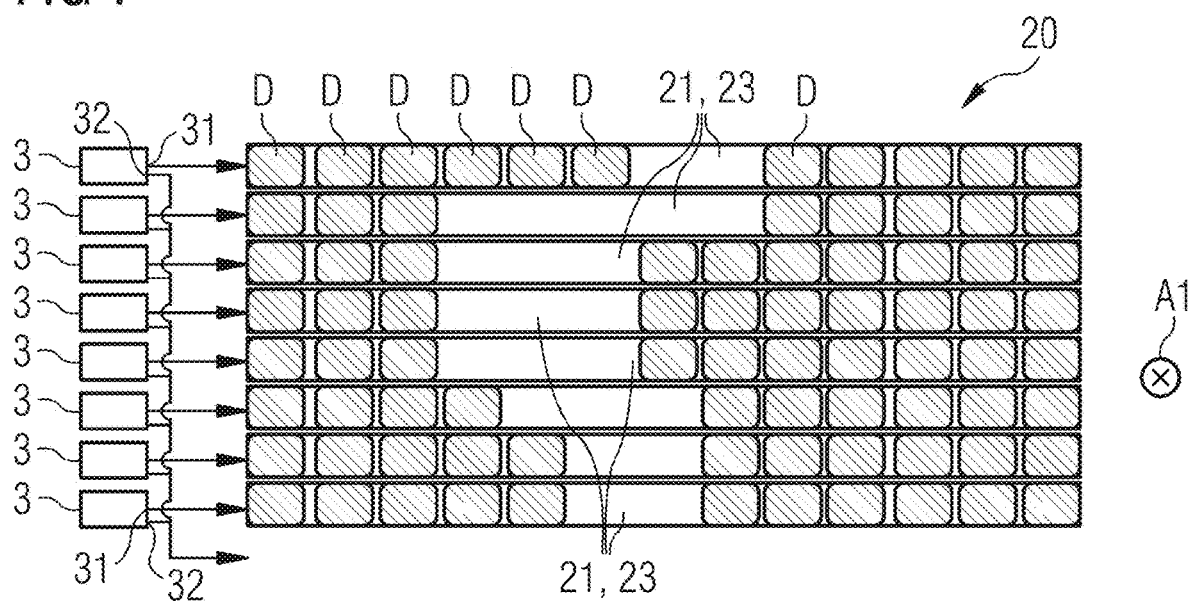
FIG. 7 shows a schematic illustration of a filter device of a filter system according to a further example embodiment of the present invention in a plan view.
Figure 8:
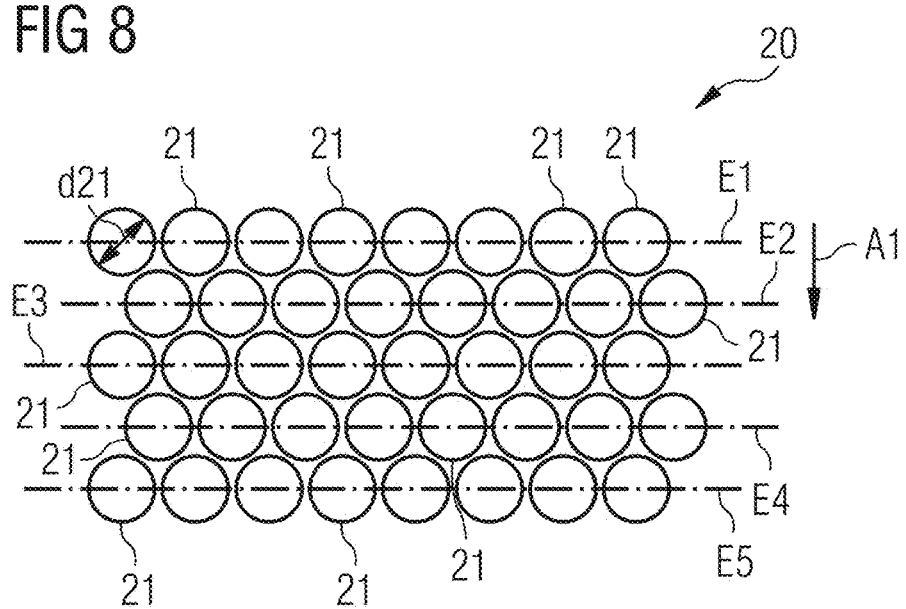
FIG. 8 shows a schematic sectional illustration of the channel arrangement of the filter device from FIG. 7.

As illustrated by way of example in FIGS. 7 and 8, the channel sections 21 of the channel arrangement 20 can also be formed by individual channels 23 in each case. It can be seen in FIG. 7 in particular that the channel sections 20 are formed by channel structures, e.g. separate tubes or lines, which run in parallel on a plane and are not interconnected. FIG. 8 shows a sectional view of the channel arrangement 20 which is illustrated schematically and purely by way of example in FIG. 7. As illustrated in FIG. 8 by way of example, the channel sections 21 can have a circular cross section in each case. A diameter d21 of the channel sections 21 can generally lie between 50 µm and 5 mm. As further illustrated in FIG. 8 by way of example, a first group of the channel sections 21 of the channel arrangement 20 is arranged on a first plane E1, a second group of the channel sections 21 of the channel arrangement 20 is arranged on a second plane E2, a third group of the channel sections 21 of the channel arrangement 20 is arranged on third plane E3, a fourth group of the channel sections 21 of the channel arrangement 20 is arranged on a fourth plane E4 and a fifth group of the channel sections 21 of the channel arrangement 20 is arranged on a fifth plane E5. The planes E1-E5 extend parallel to each other here. In general, provision can be made for one or more further groups of channel sections 21 which are arranged in each case on planes E2-E5 that are parallel to the first plane E1. In this context, the channel sections 21 of one plane can optionally be so arranged as to be offset relative to the channel sections 21 of the adjacent planes, in a direction transverse to the longitudinal extent of the channel sections 21.

Figure 9:
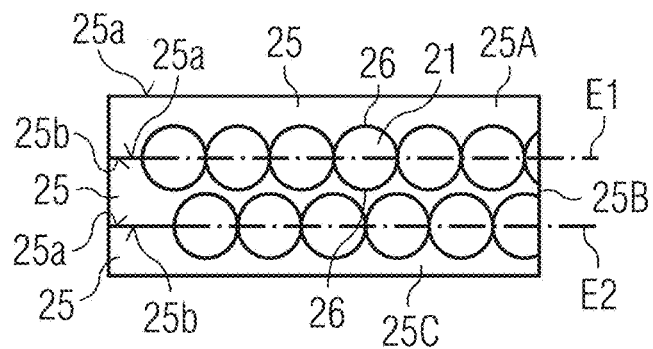
FIG. 9 shows a truncated sectional view of a channel arrangement of a filter device of a filter system according to a further example embodiment of the present invention.

FIG. 9 shows an example truncated sectional view of a channel arrangement 20 which has three plates 25 in total. The channel arrangement 20 shown by way of example has a first group of channel sections 21 which are arranged on a first plane E1, and a second group of channel sections 21 which are arranged on a second plane E2. In general, for a quantity of n groups of channel sections 21 on n planes, a quantity of n+1 plates 25 is provided. As illustrated by way of example in FIG. 9, grooves 26 extending in parallel are formed on a lower surface 25b of a first plate 25A. The lower surface 25b of the first plate 25A abuts an upper surface 25a of a second plate 25B, wherein grooves 26 are formed on the upper surface 25a of the second plate 25B, running in a manner which corresponds to the grooves 26 of the first plate 25B. The grooves 26 therefore face each other and together define the cross section and the longitudinal extent of the channel sections 21. In the case of the channel arrangement 20 illustrated by way of example in FIG. 9, the second plate 25B has further grooves 26 on a lower surface 25b, which is oriented in the opposite direction to the upper surface 25a. The lower surface 25b of the second plate 25B abuts an upper surface 25a of the third plate 25C, wherein grooves 26 are formed on the upper surface 25a of the third plate 25B, running in a manner which corresponds to the grooves 26 of the first plate 25B. Therefore the channel arrangement 20 generally has at least two plates 25 which abut each other at their surfaces 25a, 25b, wherein grooves 26 that define the channel sections 21 are formed on the surfaces 25a, 25b in each case.

Figure 10:
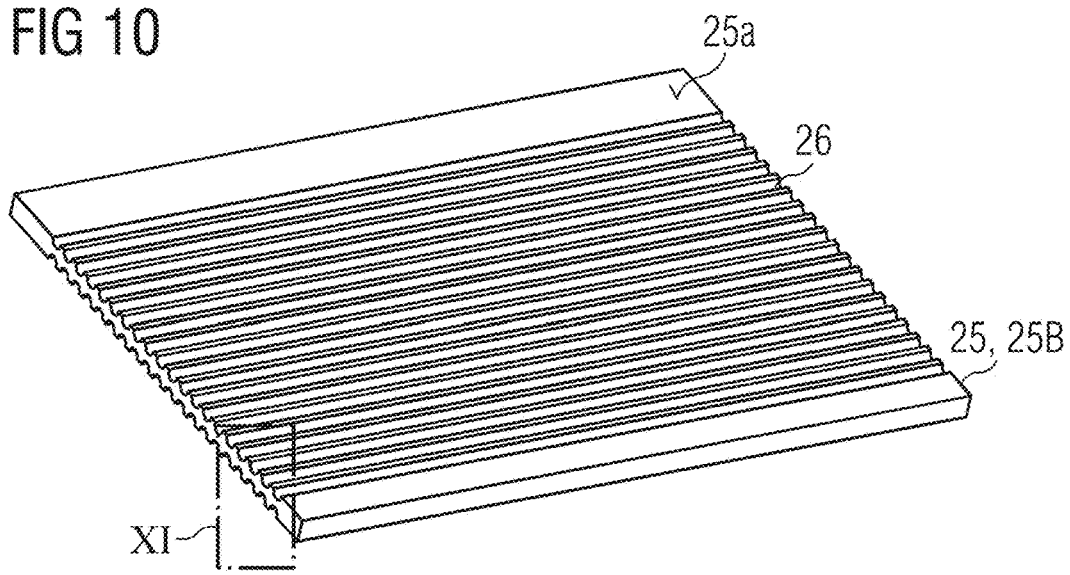
FIG. 10 shows a perspective view of a plate of the channel arrangement illustrated in FIG. 9.
Figure 11:
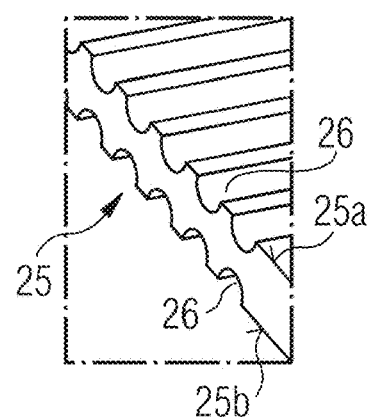
FIG. 11 shows a magnified detail view of the region designated by the letter Y in FIG. 10.

FIG. 10 shows an example plate 25, which can constitute e.g. the central plate 25B from FIG. 9. As illustrated by way of example in FIG. 10, the plate 25 can be embodied with a flat surface 25a at edge sections that are opposite each other in a transverse direction running transversely to the longitudinal extent of the grooves 26. This makes it easier to secure the plates 25 to each other, e.g. by way of bonding or adhesion. The plates 25 can be made of in particular a plastic material such as e.g. PMMA (polymethyl methacrylate), glass or other material which is largely transparent to X-radiation. FIG. 11 shows a magnified detail view of the plate 25 shown in FIG. 10. It can be seen in FIG. 11 in particular that the grooves 26 on opposite surfaces 25a, 25b of a respective plate can be so arranged as to be offset relative to each other in a direction transverse to their longitudinal extent.

The supply device 4 serves to provide a 2-phase fluid flow containing drops D of an absorber liquid that absorbs X-radiation, e.g. mercury or Galinstan, and a carrier liquid that is transparent to X-radiation, e.g. oil, in particular silicone oil. FIG. 3 shows a possible layout of the supply device 4 by way of example. The supply device 4 illustrated by way of example in FIG. 3 has a first reservoir 41, a second reservoir 42, a drop generator 6, and an optional transport device 5 with a first pump 51 and a second pump 52.

The absorber liquid is stored in the first reservoir 41. The carrier liquid is stored in the second reservoir 42. The first and second reservoirs 41, 42 are each connected to the drop generator 6 in a fluidically conductive manner. In particular, the first pump 51 is arranged in a hydraulic path between the first reservoir 41 and the drop generator 6, and the second pump 52 is arranged in a hydraulic path between the second reservoir 42 and the drop generator 6, in order to transport the liquids from the reservoirs 41, 42 to the drop generator 6. It is optionally also possible for controllable valves (not shown), e.g. magnetic valves, to be arranged between the pumps 51, 52 and the drop generator 6.

As schematically illustrated in FIG. 3, the drop generator 6 has a first input 61, a second input 62 and an output 63. The first input 61 is connected to the first reservoir 41, and the second input 62 to the second reservoir 42. The output 63 is connected to an input 30 of the sorting section 3. FIG. 4 shows a drop generator 6 which is realized as a T-piece by way of example. The drop generator 6 in this case has a first line section 61A comprising the first input 61 and second line section 62A comprising the second input 62. As illustrated schematically in FIG. 4, the first line section 61A merges transversely, preferably perpendicularly, into the second line section 62A. Since the absorber liquid and the carrier liquid cannot be mixed, the absorber liquid is cut off as a result of introducing the carrier liquid from the second line section 62A into the first line section 61A. By activating the pumps 51, 52 and/or optionally the valves in a corresponding manner, it is possible to generate a periodic sequence of drops of absorber liquid and carrier liquid in a simple manner. The drop generator 6 therefore represents a device for generating a predetermined drop sequence.

As an alternative to a drop generator 6, the supply device 4 can also have a reservoir 41 containing an emulsion of drops of the absorber liquid and the carrier liquid. The reservoir 41 can be connected to the input 30 of the sorting section 3 via the first pump 51, e.g. in a similar manner to the first reservoir 41. In order to produce a stable emulsion, a stabilizer such as e.g. PEG (polyethylene glycol) or silicone oil from which oxygen has been removed can be added to the carrier liquid.

The optional sorting section 3 is schematically illustrated in FIG. 3. The sorting section 3 has an input 30, a first output 31, a second output 32 and a deflection device 35. The input 30 of the sorting section 3 is connected to the supply device 4, e.g. to the output 63 of the drop generator 6 as illustrated by way of example in FIG. 3 or directly to the reservoir 41 if an emulsion of drops of the absorber liquid and the carrier liquid is stored in the reservoir 41. The first output 31 is connected to an input 20A of the channel arrangement 20. In the case of the filter system 1 illustrated by way of example in FIG. 3, the channel arrangement 20 takes the form of a continuous meandering channel as explained above with reference to FIG. 5. Provision is therefore made for only one sorting section 3, whose first output 31 is connected to the continuous channel. The second output 32 can be connected in particular to a separator 44 (illustrated only symbolically in FIG. 3), which is designed to separate the absorber liquid from the carrier liquid and is connected to both the first and the second reservoir 41, 42. An output 20B of the channel arrangement 20 can likewise be connected to the separator 44 as shown in FIG. 3 by way of example. A closed circuit is realized thereby, in which the 2-phase fluid flow can be transported.

In the case of the channel arrangement 20 illustrated by way of example in FIG. 7, in which the channel sections 21 are realized by individual channels 23, each channel section 21 or channel 23 is provided with a respective sorting section 3 whose first output 31 is connected to an input of the respective channel 23. The second outputs 32 of the sorting sections 3 can each be connected to the separator 44 in a similar manner to the example illustration in FIG. 3.

The deflection device 35 serves to direct individual drops D of the absorber liquid to the first output 31 or the second output 32. In this way, each channel section 21 can be supplied with a specific sequence of drops D of absorber liquid and carrier liquid. As illustrated by way of example in FIG. 3, the deflection device 35 can have a first electrode 36 and a second electrode 37 arranged opposite thereto, in order to generate an electrical field for deflecting the drops in a separation section 38 which extends between the input 30 and the outputs 31, 32 of the sorting section 3. As illustrated schematically in FIG. 3, the electrical field generated via the electrodes provokes a directional change in the movement of the drops D of absorber liquid, such that these are directed either to the first output 31 and therefore into the channel arrangement 20 or to the second output 32 and therefore optionally via the separator 44 back into the first reservoir 41. The deflection device 35 is generally designed to apply a force to the drops D, said force being transverse to the direction of flow. The sorting section therefore represents a further device for generating a predetermined drop sequence, and can be used alone or in combination with the drop generator 6.

For the purpose of locally changing the intensity of the X-radiation, the filter device 2 is arranged in the beam path 215 of the X-ray apparatus 200 as illustrated by way of example in FIG. 1. The sorting section 3 and/or the drop generator 6 is used to generate a predetermined sequence of drops D of the 2-phase fluid flow provided by the supply device 4. The drop sequences are then transported into or supplied to the channel sections 21 of the channel arrangement 20, e.g. via the hydraulic pressure that is generated by the pumps 51, 52 or by way of electrowetting by an electrode arrangement that is provided at the channel sections 21. It is alternatively also conceivable to transport the drop sequences by way of electrostatic forces generated by electrodes (not shown) that are provided at the channel sections 21. By introducing sorted sequences of drops of absorber liquid and drops of carrier material into the channel sections 21, it is possible to achieve an attenuation of the radiation at discrete points at which the drops of absorber liquid are arranged. FIG. 7 shows an arrangement of drops D of absorber liquid by way of example. The regions lying between the drop sequences are filled with carrier liquid, such that the X-radiation is attenuated only slightly or not at all in these regions.

The optional sorting device 3 can provide various sequences of drops in an efficient manner. The channel structure 20 has a simple design format and can advantageously be filled and emptied quickly, e.g. by flushing with carrier liquid. By virtue of their planar extent, a type of pixel pattern for locally resolved attenuation of the radiation can be generated by the drops of absorber material. The optional provision of a plurality of groups of channel sections 21, which are arranged on different planes E1-E5, additionally allows the degree of attenuation to be adjusted individually for each pixel.

Figure 12:
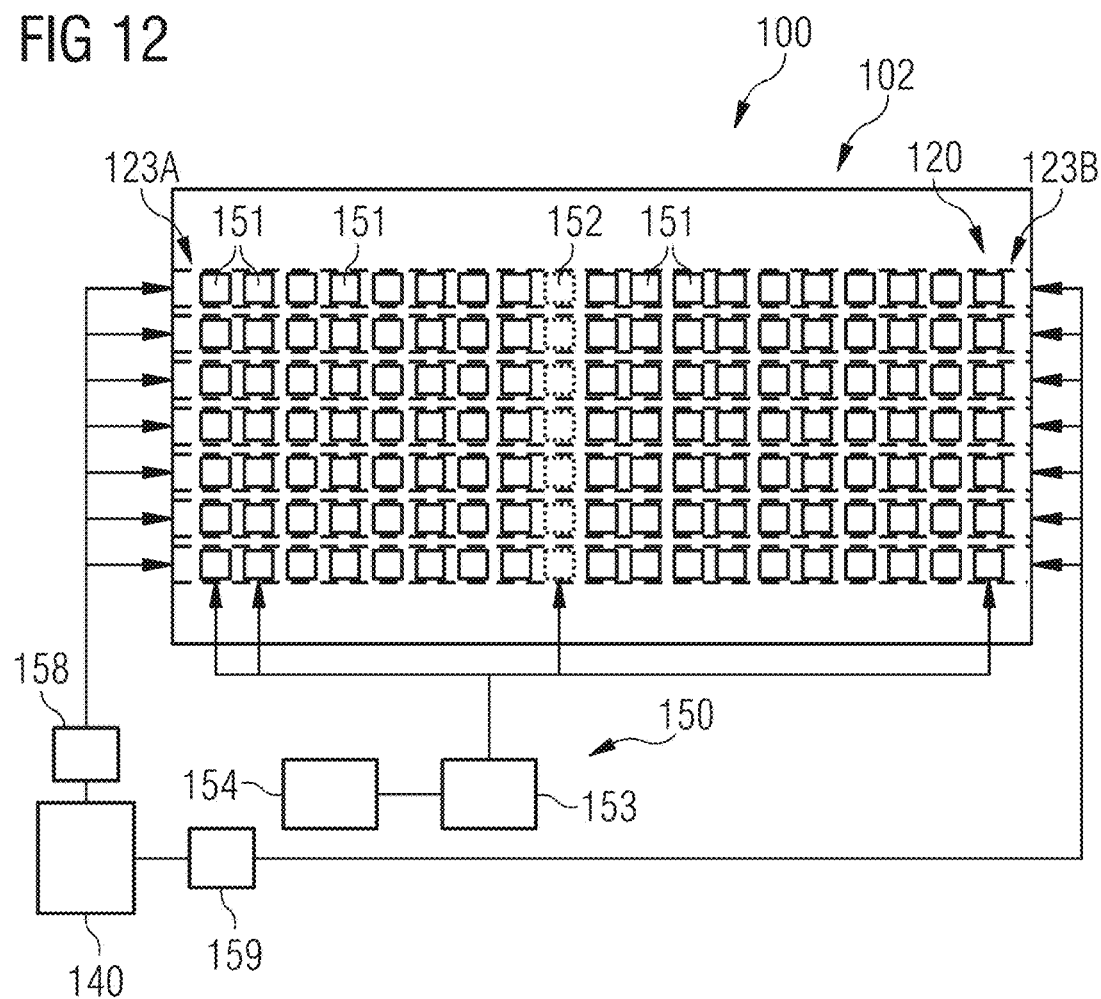
FIG. 12 shows a schematic view of a filter system according to a further example embodiment, which is not included in the present invention.

FIG. 12 shows a further filter system 100. The filter system 100 comprises a filter device 102 with a channel arrangement 120, a reservoir 140 with an absorber liquid F that absorbs X-radiation, and a transport system 150.

Figure 13:
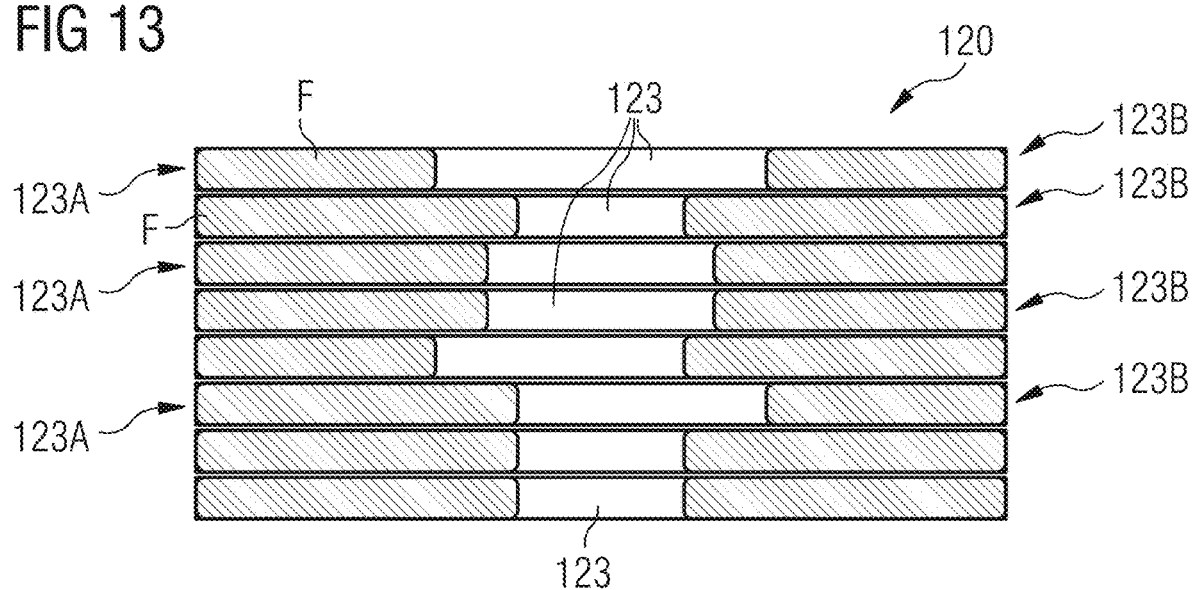
FIG. 13 shows a plan view of a channel arrangement of the filter system according to FIG. 12.

FIG. 13 shows a plan view of the channel system 120. It can be seen in FIG. 13 in particular that the channels 123 are formed by channel structures running in parallel on a plane, e.g. by separate tubes or lines which are not interconnected. Each channel 123 extends between a first end 123A and a second end 123B which is positioned opposite thereto.

Figure 14:
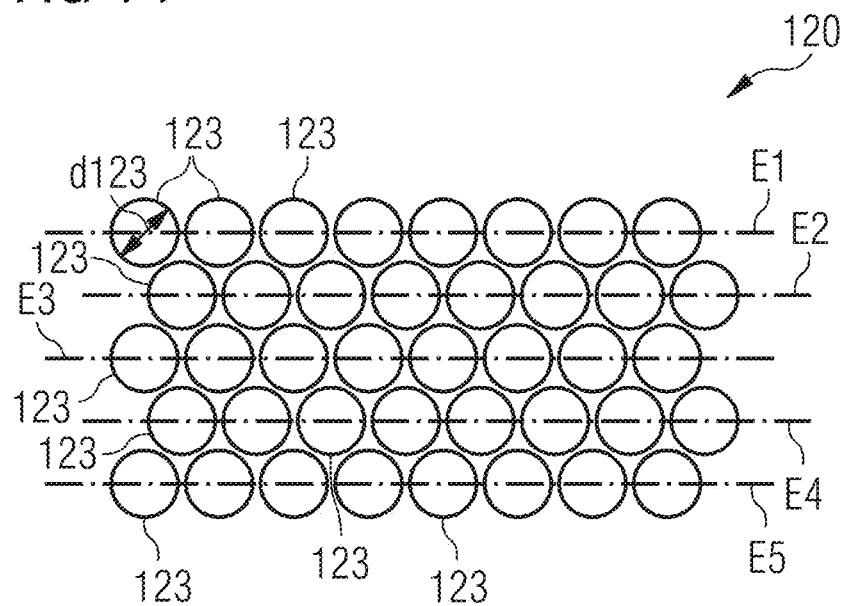
FIG. 14 shows a sectional view of the channel arrangement from FIG. 13.

FIG. 14 shows a sectional view of the channel arrangement 120 which is illustrated schematically and purely by way of example in FIG. 13. As illustrated by way of example in FIG. 14, the channels 123 can have a circular cross section in each case. A diameter d123 of the channels 123 can generally lie between 50 μm and 5 mm. As also illustrated by way of example in FIG. 14, a first group of the channels 123 of the channel arrangement 120 is arranged on a first plane E1, a second group of the channels 123 of the channel arrangement 120 is arranged on a second plane E2, a third group of the channels 123 of the channel arrangement 120 is arranged on a third plane E3, a fourth group of the channels 123 of the channel arrangement 120 is arranged on a fourth plane E4 and a fifth group of the channels 123 of the channel arrangement 120 is arranged on a fifth plane E5. The planes E1-E5 extend parallel to each other here. In general, provision can be made for one or more further groups of channels 123 which are arranged in each case on planes E2-E5 that are parallel to the first plane E1. In this context, the channels 123 of one plane can optionally be so arranged as to be offset relative to the channels 123 of the adjacent planes, in a direction transverse to the longitudinal extent of the channels 123, as illustrated by way of example in FIG. 14. The individual channels 123 can be realized via plates 25 with grooves 26 which are formed therein, e.g. as illustrated in FIG. 9 and explained above.

The reservoir 140 in FIG. 12 is illustrated merely symbolically as a block and contains an absorber liquid which absorbs X-radiation, e.g. Galinstan or mercury. For example, an electrolyte can be added to the absorber liquid. The reservoir 140 is connected to the channel arrangement 120 in a fluidically conductive manner, e.g. via a line system, each channel 123 being connected to the reservoir 140 at both the first end 123A and the second end 123B.

As schematically illustrated in FIG. 12, the transport system 150 can take the form of an electrode arrangement. In the filter system 100 illustrated by way of example in FIG. 12, the electrode arrangement has a multiplicity of first electrodes 151 and at least one second electrode 152 per channel 123. For each channel 123, a multiplicity of first electrodes 151 are so arranged as to be distributed along the channel 123, e.g. fastened to an outer surface of the channels 123, in order to apply a first electrical potential to the channel walls. The first electrodes 151 are electrically insulated from the absorber liquid, e.g. by virtue of the channels 123 being made of an electrically insulating material. For each channel 123, at least one second electrode 152 is arranged in the interior of the respective channel 123 and applies a second electrical potential to the absorber liquid F.

A switch device 153 is electrically connected to the first electrodes 151 or is designed to connect each of the first electrodes 151 individually to an electrical voltage source 154 and optionally to control the electrical potential of the first electrodes 151. The switch device 153 is optionally also connected to the second electrodes 152, in order to control their electrical potential. Alternatively, the second electrodes 152 can also be coupled to a ground potential. The switch device 153 is designed to connect the individual first electrodes 153 consecutively to the voltage source 154, whereby transportation of the absorber fluid along the channels is achieved.

Alternatively, the transport system 150 can also be realized via a hydraulic system. The hydraulic system comprises at least one pump, which is arranged between the reservoir 123 and the channel arrangement 120 in order to fill the channels 123 from two sides with a specific occupancy level of absorber liquid F. A hydraulic system comprising a first pump 158, which is arranged between the reservoir 140 and the first ends 123A of the channels 123, and a second pump 159, which is arranged between the reservoir 140 and the second ends 123B of the channels 123, is illustrated in FIG. 12 by way of example. It is also conceivable to provide one or two dedicated pumps for each of the channels 123. Alternatively or additionally, valves can be provided in order to control the occupancy level of absorber liquid in the channels.

Although the invention is illustrated and described in detail by the example embodiments above, the invention is not restricted by the examples disclosed therein, and other variations may be derived therefrom by a person skilled in the art without thereby departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A filter system for local attenuation of X-radiation, comprising:

a filter device, arranged in a beam path of an X-ray apparatus and including a channel arrangement, the channel arrangement including a multiplicity of channel sections extending in parallel on a plane;

a supply device to provide a 2-phase fluid flow containing drops of an absorber liquid, to absorb X-radiation and a carrier liquid transparent to X-radiation; and a sorting section, including an input connected to the supply device, a first output connected to the channel arrangement, a second output, and a deflection device to direct individual drops of the absorber liquid to the first output or the second output.

2. The filter system of claim 1, wherein the channel sections of the channel arrangement are connected to each other via connecting sections so as to form a continuous channel.

3. The filter system of claim 2, wherein the channel sections of the channel arrangement are each formed by individual channels, each connected to the supply device.

4. The filter system of claim 2, wherein a first group of the channel sections of the channel arrangement is arranged on a first plane and one or more further groups of channel sections are provided, each of the one or more further groups of channel sections being arranged on planes parallel to the first plane.

5. The filter system of claim 2, wherein the channel arrangement includes at least two plates, a surface of each of the at least two plates abutting a surface of another of the at least two plates, and wherein grooves defining the channel sections are formed on surfaces of the at least two plates.

6. The filter system of claim 2, wherein the supply device includes a first reservoir containing the absorber liquid, a second reservoir containing the carrier liquid, and a drop generator to generate the 2-phase fluid flow, and wherein the drop generator is connected via a first input to the first reservoir and via a second input to the channel arrangement.

7. The filter system of claim 6, wherein the drop generator includes a first line section including the first input and a second line section including the second input, and wherein the first line section and the second line sections merge in a T-shaped junction.

8. An X-ray apparatus, comprising:
an X-ray source to generate and emit X-radiation in a beam path;
an X-ray detector, arranged in the beam path; and
the filter system of claim 2, wherein the filter device of the filter system is arranged in the beam path, between the X-ray source and the X-ray detector.

9. The filter system of claim 1, wherein the channel sections of the channel arrangement are each formed by individual channels, each connected to the supply device.

10. The filter system of claim 1, wherein a first group of the channel sections of the channel arrangement is arranged on a first plane and one or more further groups of channel sections are provided, each of the one or more further groups of channel sections being arranged on planes parallel to the first plane.

11. The filter system of claim 1, wherein the channel arrangement includes at least two plates, a surface of each of the at least two plates abutting a surface of another of the at least two plates, and wherein grooves defining the channel sections are formed on surfaces of the at least two plates.

12. The filter system of claim 1, wherein the supply device includes a first reservoir containing the absorber liquid, a second reservoir containing the carrier liquid, and a drop generator to generate the 2-phase fluid flow, and wherein the drop generator is connected via a first input to the first reservoir and via a second input to the channel arrangement.

13. The filter system of claim 12, wherein the drop generator includes a first line section including the first input and a second line section including the second input, and wherein the first line section and the second line sections merge in a T-shaped junction.

14. The filter system of claim 1, wherein the supply device includes a reservoir containing an emulsion of drops of the absorber liquid and the carrier liquid, and wherein the reservoir is connected to the channel arrangement.

15. The filter system of claim 1, wherein the absorber liquid is mercury or Galinstan, and wherein the carrier liquid is oil.

16. The filter system of claim 15, wherein the oil is silicone oil.

17. An X-ray apparatus, comprising:
an X-ray source to generate and emit X-radiation in a beam path;
an X-ray detector, arranged in the beam path; and
the filter system of claim 1, wherein the filter device of the filter system is arranged in the beam path, between the X-ray source and the X-ray detector.

18. A method for locally changing intensity of X-radiation, the method comprising:
generating sequences of drops from a 2-phase fluid flow containing drops of an absorber liquid, to absorb X-radiation and a carrier liquid, transparent to X-radiation; and
supplying the sequences of drops generated into channel sections of a channel arrangement of a filter device, arranged in a beam path between an X-ray source and an X-ray detector, wherein the channel arrangement includes a multiplicity of channel sections extending in parallel on a plane.

* * * * *